United States Patent [19]

Fan et al.

[11] Patent Number: 5,763,629
[45] Date of Patent: Jun. 9, 1998

[54] ALKOXYLATED GLYCIDYL (METH) ACRYLATES AND METHOD OF PREPARATION

[75] Inventors: Mingxin Fan, West Chester; Gary W. Ceska, Exton; James Horgan, West Chester; Thomas W. Hazell, Exton, all of Pa.

[73] Assignee: Sartomer Company, Exton, Pa.

[21] Appl. No.: 772,979

[22] Filed: Dec. 23, 1996

[51] Int. Cl.$^6$ ................................................. C07D 301/12
[52] U.S. Cl. ............................................ 549/531; 549/548
[58] Field of Search ......................................... 549/531, 548

[56] References Cited

U.S. PATENT DOCUMENTS

| | | | |
|---|---|---|---|
| 5,324,803 | 6/1994 | Sawada et al. | 526/279 |
| 5,481,012 | 1/1996 | Caubers et al. | 549/531 |

Primary Examiner—C. Warren Ivy
Assistant Examiner—Lyman H. Smith
Attorney, Agent, or Firm—James A. Drobile; Michael B. Fein

[57] ABSTRACT

Compounds of the formula

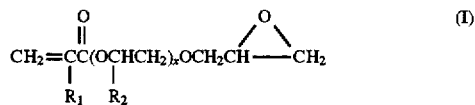

(I)

wherein $R_1 =$ H, $CH_3$;

$R_2 =$ H, $(C_1-C_6)$alkyl; and $x = 1-20$; and process for preparing such compounds by reacting a compound of the formula

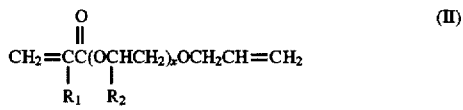

(II)

with hydrogen peroxide in the presence of (a) tungstic acid or its metal salts, (b) phosphoric acid or its metal salts, and (c) at least one phase transfer catalyst.

17 Claims, No Drawings

ALKOXYLATED GLYCIDYL (METH) ACRYLATES AND METHOD OF PREPARATION

BACKGROUND OF THE INVENTION

1. Field of the Invention

This invention relates to a new class of acrylates and methacrylates, hereinafter "(meth)acrylates," containing epoxide functionalities and methods for their preparation.

2. Description of the Prior Art

Glycidyl (meth)acrylate, having two different polymerizable functional groups, is widely used as a chemical intermediate. The (meth)acrylate group can be polymerized or copolymerized into a polymer backbone while the epoxide functional group is kept intact which then can be further modified. Currently, glycidyl methacrylate is produced from epichlorohydrin and sodium methacrylate salt. Sodium chloride is generated as by product which is contaminated with epichlorohydrin. Epichlorohydrin is a very toxic material, and most working places are not equipped to handle it. Epichlorohydrin is present in the final glycidyl (meth) acrylate product even after normal purification. Glycidyl methacrylate itself has a low boiling point and is fairly volatile and toxic.

Epoxidation of unsaturated organic compounds has been known for sometime to generate epoxide groups. Olefins can be epoxidized with a number of peracids and peroxides, such as trifluroperacetic acid (J. Am. Chem. Soc. 1955, 77, 89) and t-butyl peroxide (J. Am. Chem. Soc. 1980, 102, 5974).

Hydrogen peroxide is a very attractive and economical oxidant industrially since the only by product generated is water. Epoxidation using hydrogen peroxide in the presence of metal catalysts has been known for some time. U.S. Pat. Nos. 2,833,787 and 2,833,788 describe the epoxidation of unsaturated alcohol with hydrogen peroxide and sodium pertungstate. Unsaturated acids have been epoxidized using hydrogen peroxide and sodium tungstate. (J. Org. Chem. Vol. 52, 1868 and vol 53, 3582). Molybdenum and hydrogen peroxide have also been used for the peroxidation of olefins (Angew. Chem. Int. Ed. Engl. 1982, 21, 734–750). Under phase transfer catalysis conditions, water soluble alkali metal tungstate and hydrogen peroxide have been used to epoxidize olefins in the presence of excess of olefins (J. Org. Chem. 1985, 50, 2688–2690). Heteropolyacids have been also used in combination of hydrogen peroxide to epoxidize olefins (J. Org. Chem. 1987, 52, 1868–1870; J. Org. Chem. 1988, 53, 3587–3593).

Epoxidation of vinyl norbornene (meth) acrylate at 50° C. using peracetic acid has been reported (U.S. Pat No. 3,459, 775); the final yield is very low and normally less than 42%. Japanese patent application JP-A-62/81 378 describes the epoxidation of dicyclopentenyloxyethyl acrylate at 60° C. using 35% hydrogen peroxide with less than 48% yield.

U.S. Pat. Nos. 5,283,360 and 5,510,516 to Cauhere, et al. show epoxidation of unsaturated (meth)acrylate esters with hydrogen peroxide using a catalyst system which comprises alkali metal salts of tungstic or molybdinic acids and a heteropolyacid. Cauhere et al do not show (meth)acrylates which have been alkoxylated, nor do they show phosphoric acid.

GB application 2 0558212A by Venturello, et al. shows epoxidation of olefins with hydrogen peroxide using a catalyst system consisting of W, Mo, or V, and at least one derivative of P or As. This application does not show epoxidation of (meth)acrylates or alkoxylated compounds.

SUMMARY OF THE INVENTION

This invention relates to a new class of monomers of the formula

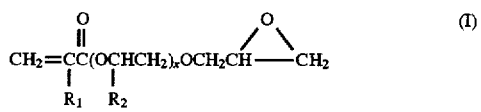

wherein $R_1$=H, $CH_3$;

$R_2$=H, ($C_1$–$C_6$)alkyl; and $x$=1–20;

and also oligomers thereof, and to a method for making the new monomers and oligomers.

This invention also comprises a process for preparing such compounds by reacting a compound of the formula

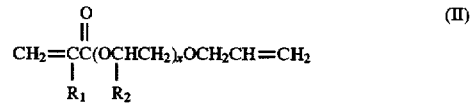

with hydrogen peroxide in the presence of (a) tungstic acid or its metal salts, (b) phosphoric acid or its metal salts, (c) at least one phase transfer catalyst.

DETAILED DESCRIPTION OF INVENTION AND PREFERRED EMBODIMENTS

The compounds of the invention are useful as monomers, and are glycidyl (meth)acrylate derivatives with higher molecular weight than glycidyl (meth)acrylate. They have utility as chemical intermediates where the additional polyether group is advantageous.

An advantage of the process of the invention for the preparation the monomers is that it does not involve epichlorohydrin which is very toxic. The process involves only a low level of catalyst composition and no organic and/or peracid, which results in simple product workup and process. The new catalyst composition is highly effective and efficient. The epoxidation of the alkoxylated allyl (meth) acrylate compounds of formula II is carried out with hydrogen peroxide in the presence of tungstic acid or its metal salts, phosphoric acid or its metal salts, and phase transfer catalyst can be performed at any temperature which is sufficient to react, however, particularly suitable temperatures are between 0° C. and 100° C., preferably from 25° C. to 70° C. The reaction takes place faster at higher temperature and requires shorter time to complete. The reaction is typically exothermic and slow addition of hydrogen peroxide is preferred to control the exotherm. At higher temperature hydrogen peroxide undergoes decomposition. The reaction can be performed at pressures from subatmospheric to superatmospheric pressures; however, the reaction is preferably carried out at atmospheric pressure.

The compounds of formula II can be prepared according to known methods, for example the method shown in U.S. Pat. No. 4,618,703 to Ceska.

The epoxidation can be performed with or without solvent, but solvent is preferred to reduce the viscosity. Suitable solvents are water immiscible organic solvent such as chlorinated hydrocarbons, ethers, glycol ethers, hydrocarbons, or combinations thereof can be used. Particular suitable organic solvents are toluene, chlorobenzene, chloroform, methylene chloride, heptane and the like.

Hydrogen peroxide solution is used as oxidant in the concentration of 5 to 70%. The amount of hydrogen peroxide can vary depending on the desired degree of epoxidation, typically from 0.1 to 1.5 equivalent per unsaturated double bond.

The phase transfer catalyst can be used from 0.001 to 1, preferably 0.05 to 0.1, equivalents per equivalent of carbon-carbon double bond in the compound of formula II. Suitable phase transfer catalysts includes quaternary ammonium salts, quaternary phosphonium salts, polyethers, and the like. Examples of phase transfer catalysts include, for example, trioctylmethylammonium chloride, trioctylmethylammonium bromide, trioctylmethylammonium iodide, trioctylmethylammonium hydrogen sulfate, trioctylmethylammonium nitrate, tetrahexylammonium chloride, tetrahexylammonium bromide, tetrahexylammonium iodide, tetrahexylammonium hydrogen sulfate, tetrahexylammonium nitrate, tetrabutylammonium chloride, tetrabutylammonium bromide, tetrabutylammonium nitrate, tetrabutylammonium hydrogen sulfate, dioctadecyldimethylammonium chloride, dioctadecyldimethylamnionium bromide, dioctadecyldimethylammonium nitrate, dioctadecyldimethylammonium hydrogen sulfate, dihexadecyldimethylammonium chloride, dihexadecyldimethylammonium bromide, dihexadecyldimethylammonium nitrate, dihexadecyldimethylammonium hydrogen sulfate, trioctylmethylphosphonium chloride, trioctylmethylphosphonium bromide, trioctylmethylphosphonium nitrate, trioctylmethylphosphonium hydrogen sulfate, tetrahexylphosphonium chloride, tetrahexylphosphonium bromide, tetrahexylphosphonium nitrate, tetrahexylphosphonium hydrogen sulfate, tetrabutylphosphonium chloride, tetrabutylphosphonium bromide, tetrabutylphosphonium nitrate, tetrabutylphosphonium hydrogen sulfate, tetrabutylphosphonium iodide, dioctadecyldimethylphosphonium chloride, dioctadecyldimethylphosphonium bromide, dioctadecyldimethylphosphonium nitrate, dioctadecyldimethylphosphonium hydrogen sulfate, dihexadecyldimethylplhosphonium chloride, dihexadecyldimethylphosphonium bromide, dihexadecyldimethylphosphonium nitrate, dihexadecyldimethylphosphonium hydrogen sulfate, tetraalkylammonium hydroxide, tetraalkylammonium tribromide, tetraalkylammonium trifluoromethanesulfonate, and any combination thereof. Phosphoric acid or its various salts can be used from 0.001 to 1, preferably 0.05 to 0.1, equivalents per equivalent of carbon-carbon double bond in the compound of formula II. Sodium or potassium salts of monobasic, dibasic, or tribasic salts of phosphoric acid can also be used. The final pH can be adjusted by other acids or bases to 0–5.

Tungstic acid can be used as the metal catalyst. The metal salts are water soluble and the acid is not. The typical amount of metal catalyst is used from 0.005 to 5%, preferably about 0.1 to 1%, based on compound of formula II. The preferred catalyst is tungstic acid which is not water soluble.

The epoxidized unsaturated (meth)acrylates can be used in a variety of applications, such as coatings, epoxy/amine cure, cationic cure/free radical hybrid cure, and as chemical intermediates for polymers.

EXAMPLES

The following non-limiting examples are presented to illustrate a few embodiments of the invention. All parts and percentages are by weight unless otherwise indicated.

Example 1

Synthesis of Propoxylated Allyl Methacrylate (5 PO) of Formula II

Propoxylated allyl alcohol (5 propylene oxide units per molecule (1344.8 g), methacrylic acid (448.5 g), 4-methoxyphenyl (6.75 g), methanesulfonic acid (70%, 33.75 g), and heptane (405.0 g) were added to a reactor and stirred at room temperature, with air sparge being applied. The mixture was heated to reflux while water generated was removed via azeotrope. After the reaction was complete (no more water formation) the mixture was neutralized with 25% NaOH and washed twice with 25% NaOH. The final product, propoxylated allyl methacrylate, was obtained by removing the heptane solvent under reduced pressure. Yield was 1532.4 grams.

Example 2

Synthesis of propoxylated allyl methacrylate (2 PO) of Formula II

Example 1 was repeated using 2 PO allyl alcohol. Allyl methacrylate having 2 propylene oxide groups per molecule was obtained.

Example 3

Epoxidation of propoxylated allyl methacrylate (5 PO)

100.0 g unsaturated propoxylated allyl methacrylate ester from Example 1 was dissolved into 100.0 g toluene. Then 2.7 g {MeN[(CH$_2$)$_7$CH$_3$]$_3$ {PO$_4$[WO(O$_2$)$_2$]$_4$} was added to the solution. The solution was stored and heated to 60° C. followed by slow addition of 50.0 ml H$_2$O$_2$ (30%) in 30 min. After 22.0 hours, the reaction mixture was analyzed by GC, which showed 85% conversion to epoxide.

Example 4

Epoxidation of propoxylated allyl methacrylate (5 PO)

3.0 g H$_2$WO$_4$, 1.5 g NaOH (25%), and 1.5 g H$_3$PO$_4$ (85%) were added to a reactor at room temperature. Then 200.0 g propoxylated allyl methacrylate (5 PO) ester produced according to Example 1, 200.0 g toluene, and 3.0 g trioctyl methyl ammonium chloride were added. The mixture was stirred and heated to 60° C. for 23 hours. GC analysis showed complete epoxidation to propoxylated glycidyl methacrylate.

While the invention has been described in sufficient detail for those skilled in the art to make and use it, various modifications, alternatives, and improvements should become readily apparent without departing from the spirit and scope of the invention as set forth in the following claims.

What is claimed is:

1. Compounds of the formula

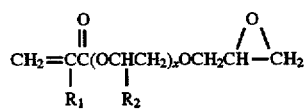

wherein $R_1$=H, CH$_3$;

$R_2$=H, (C$_1$–C$_6$)alkyl; and x=1–20 provided that when $R_2$ is H, x is greater than 10.

2. Compounds according to claim 1 wherein $R_2$ is CH$_3$ and x=2 to 5.

3. Compounds according to claim 1 wherein $R_1$=CH$_3$; and $R_2$=CH$_3$.

4. Process for preparing compounds according to claim 1 comprising reacting an alkoxylated allyl acrylate or methacrylate of the formula

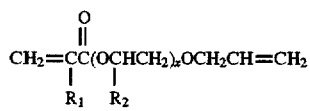

(II)

wherein
$R_1$=H, $CH_3$;
$R_2$=H, ($C_1$–$C_6$) alkyl; and
x=1–20;
with hydrogen peroxide in the presence of (a) tungstic acid, (b) phosphoric acid or its metal salts, and (c) at least one phase transfer catalyst.

5. Process according to claim 4 wherein said hydrogen peroxide is introduced in an amount of about 0.1 to 1.5 equivalent per equivalent of allyl double bond.

6. Process according to claim 4 wherein the reaction is conducted at a temperature of about 0° C. to 100° C.

7. Process according to claim 4 wherein the reaction is conducted at a temperature of about 25° C. to 70° C.

8. Process according to claim 4 wherein the phase transfer catalyst is present in an amount of about 0.001 to 1 equivalents per equivalent of allyl double bond in the compound of formula II.

9. Process according to claim 4 wherein the phase transfer catalyst is present in an amount of about 0.05 to 0.1 equivalents per equivalent of allyl double bond in the compound of formula II.

10. Process according to claim 4 wherein the phase transfer catalyst is selected from the group consisting of quaternary ammonium salts, quaternary phosphonium salts, and polyethers.

11. Process according to claim 4 wherein the reaction is conducted in the presence of a water immiscible organic solvent.

12. Process according to claim 4 wherein the reaction is conducted in the presence of a water immiscible organic solvent selected from the group consisting of chlorinated hydrocarbons, ethers, glycol ethers, hydrocarbons, and combinations thereof.

13. Process according to claim 10 wherein the solvent is selected from the group consisting of toluene, chlorobenzene, chloroform, and methylene chloride.

14. Process according to claim 4 wherein the phosphoric acid or phosphoric acid salt comprises about 0.001 to 0.5 equivalents per equivalent of allyl double bond of the compound of formula II.

15. Process according to claim 4 wherein the phosphoric acid or salt thereof is a sodium or potassium salt of monobasic, dibasic, or tribasic phosphoric acid.

16. Process according to claim 4 wherein the pH of the reaction is adjusted by acids or bases to about 0–5.

17. Process according to claim 4 wherein the tungstic acid is present in and amount of about 0.005 to 5% based on weight of compound of formula II.

* * * * *